(12) United States Patent
Van De Bovenkamp-Bouwman et al.

(10) Patent No.: US 7,078,553 B2
(45) Date of Patent: Jul. 18, 2006

(54) KETONE PEROXIDE DERIVATIVES, THEIR PREPARATION AND USE

(75) Inventors: Anna Gerdine Van De Bovenkamp-Bouwman, Nijkerk (NL); Joachim Willem J. Van Gendt, Luttenberg (NL); John Meijer, Deventer (NL); Andreas Herman Hogt, Enschede (NL); Andreas Petrus Van Swieten, Velp (NL)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 10/417,313

(22) Filed: Apr. 16, 2003

(65) Prior Publication Data

US 2004/0260111 A1 Dec. 23, 2004

Related U.S. Application Data

(63) Continuation of application No. 09/581,599, filed as application No. PCT/EP98/08129 on Dec. 10, 1998, now Pat. No. 6,552,215.

(30) Foreign Application Priority Data

Dec. 18, 1997 (EP) .................................. 97203987

(51) Int. Cl.
*C07C 69/96* (2006.01)

(52) U.S. Cl. ...................................... 558/263; 560/302

(58) Field of Classification Search ................ 558/263; 560/302
See application file for complete search history.

(56) References Cited

U.S. PATENT DOCUMENTS 4,443,376 A 4/1984 Pastorino et al. ........... 260/453

FOREIGN PATENT DOCUMENTS

EP 043 402 A1 1/1982
JP 48043491 * 12/1993

OTHER PUBLICATIONS

Data Base WPI: Accession No.: 1970:78579 (CAPLUS), Abstract of J. Org. Chem. by Robertson et al., 35(2), pp. 545-547, 1970.
Data base WPI: Accession No.: 1974:145441 (CAPLUS), Abstract of JP 48043491 B4, 1974.
Derwent Abstract XP-002065312 abstracting Japanese Patent No. J74048928.
Derwent Abstract XP-002065313 abstracting Japanese Patent No. J73043491.
Robertson et al., "Diphenylmethyl Bishydroperoxide. An Anomalous Product from the Ozonolysis of Tetraphenylethylene," Journal of Applied Polymer Science, vol. 35, pp. 545-547 (1970).
Xie, et al., "Experimental Investigation of Vinyl Chloride Polymerization at High Conversion—Conversion and Tracer Response Relationships," Journal of Applied Polymer Science, vol. 41, pp. 2327-2347, (1990).

* cited by examiner

*Primary Examiner*—Johann Ritcher
*Assistant Examiner*—Chukwuma Nwaonicha
(74) *Attorney, Agent, or Firm*—Richard P. Fennelly; Michelle J. Burke; Louis A. Morris

(57) ABSTRACT

The invention relates to peroxides derivable from

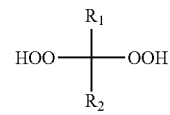

The invention further relates to the process to make these peroxides as well as to their use in polymerization, curing, and modification reactions.

19 Claims, No Drawings

KETONE PEROXIDE DERIVATIVES, THEIR PREPARATION AND USE

This application is a continuation application of U.S. Ser. No. 09/581,599 filed Sep. 5, 2000 now U.S. Pat. No. 6,552,215, which was filed pursuant to 35 U.S.C. 371, based on International Application No. PCT/EP98/08129, filed Dec. 10, 1998, and claims priority of EPO Application No. 97203987.9, filed Dec. 18, 1997.

The present invention relates to a preparation process for peroxides derivable from

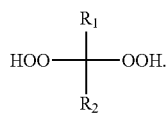

It also relates to particular peroxides so obtainable and their use. More specifically, the present invention relates to the preparation process of peroxy esters and peroxy carbonates and mixed diperoxides, and to specific monoperoxy carbonates, diperoxy esters, diperoxy carbonates, and mixed diperoxides. Finally, the present invention relates to the use of these peroxides as polymerization initiators, curing agents for unsaturated polyesters, and modifying agents, and to formulations comprising these peroxides.

EP-A-0 043 402 discloses the production of symmetrical diperoxy esters by reacting an acid chloride with a ketone hydroperoxide in a two-phase solvent system comprising an apolar solvent. A monoperoxy ester is obtained as by-product in this reaction. If so desired, the diperoxy ester can be separated from the mixture and utilized in the pure form. A similar process is disclosed in JP-A-49-48928.

JP-A-48-43491 discloses a similar method for the production of diperoxy carbonates.

Because these prior art preparation processes do not result in the formation of monoperoxy ester or monoperoxy carbonate as a major constituent, it is impossible to produce asymmetrical diperoxy esters and diperoxy carbonates and mixed peroxides in a controlled manner.

It is an object of the present invention to provide a preparation process such that the monoperoxy ester or monoperoxy carbonate is a major constituent in the reaction mixture. A major constituent is generally present in an amount of at least about 50% of the formed peroxy esters and peroxy carbonates. Preferably, the amount is above 70%, such as 80% or 90%. Generally, the amount of monoperoxy ester or monoperoxy carbonate is in the range 50%–90%, in particular 70%–90%, such as 75%–85%. Below it will be shown that the relative amount of monoperoxy ester and monoperoxy carbonate can be adjusted as desired by the selection of proper reaction constituents and reaction conditions When the objective is to prepare symmetrical and/or asymmetrical diperoxy esters and diperoxy carbonates and mixed peroxides as well as their mixtures, these end products are formed in an amount of at least 90%, in general at least 95%, in particular at least 99%.

The present invention is based on the insight that by a proper selection of the solvents for the inert two-phase solvent system, in particular of the polar solvents, monoperoxy ester and monoperoxy carbonate are formed as a major constituent in the reaction mixture.

Accordingly, the present invention provides a process for the preparation of monoperoxy ester or monoperoxy carbonate having the general formula I:

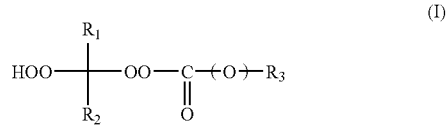

wherein $R_1$ and $R_2$ are independently selected from the group comprising hydrogen, $C_1$–$C_{20}$ alkyl, $C_3$–$C_{20}$ cycloalkyl, $C_6$–$C_{20}$ aryl, $C_7$–$C_{20}$ aralkyl, and $C_7$–$C_{20}$ alkaryl, which groups may include linear or branched alkyl moieties; and each of $R_1$ and $R_2$ may optionally be substituted with one or more groups selected from hydroxy, alkoxy, linear or branched alkyl, aryloxy, halogen, ester, carboxy, nitrile, and amido, and $R_3$ is independently selected from the group comprising $C_1$–$C_{20}$ alkyl, $C_3$–$C_{20}$ cycloalkyl, $C_6$–$C_{20}$ aryl, $C_7$–$C_{20}$ aralkyl, and $C_7$–$C_{20}$ alkaryl, which groups may include linear or branched alkyl moieties; and $R_3$, may optionally be substituted with one or more groups selected from hydroxy, alkoxy, linear or branched alkyl, aryloxy, halogen, ester, carboxy, nitrile, and amido, comprising the reaction of the corresponding T4-ketone peroxide with the general formula II:

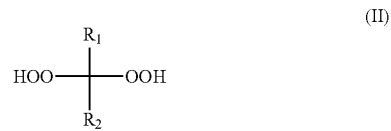

wherein $R_1$ and $R_2$ have the identified meaning, with an acid halogen or halogen formate with the general formula III:

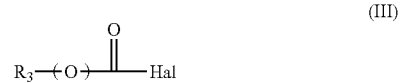

wherein $R_3$ has the identified meaning, in an inert two-phase solvent system comprising polar solvents.

The inert two-phase solvent system according to the present invention comprises two polar solvents. Preferably, one of the solvents is an aqueous alkali comprising-phase and the other solvent is a polar organic solvent which is not miscible with the other (aqueous) phase. A solvent is a polar solvent when its dipole moment is larger than 0D, in other words, has a certain polarity. The polarity increases proportionally with the value of the dipole moment (D). For a definition and explanation of the dipole moment reference is made to R. C. Reid, J. M. Prausnitz, B. E. Poling, *The Properties of Gases & Liquids,* 4th edition, 1988, ISBN 0-07-051799-1 (Ref.1) and John A. Dean, *Lange's Handbook of Chemistry,* 13th edition, 1985, ISBN 0-07-016192-5 (Ref.2).

The following Table 1 provides a listing of the dipole moments of various solvents.

TABLE 1

Dipole moments of various solvents.

| Solvent | Dipole moment (D) (Ref. 1) | Dipole moment (D) (Ref. 2) |
| --- | --- | --- |
| Acetonitrile | 3.5 | 3.92 |
| Cyclohexanone | 3.1 | 3.01 |
| Acetone | 2.9 | 2.88 |
| Acetic anhydride | 3.0 | 2.80 |
| Water | 1.8 | 1.84 |
| Butylacetate | 1.8 | 1.86 |
| Ethylacetate | 1.9 | 1.81 |
| Acetic acid | 1.3 | 1.74 |
| Methanol | 1.7 | 1.70 |
| Ethanol | 1.7 | 1.69 |
| n-Butanol | 1.8 | 1.66 |
| Dichloromethane | 1.8 | 1.46 |
| Dichloroethane | 1.8 | 1.20 |
| Diethyl ether | 1.3 | 1.15 |
| Chloroform | 1.1 | 1.01 |
| 1,4-Dioxane | 0.4 | 0 |
| n-Butane | 0 | 0 |
| Methane | 0 | 0 |
| Methylethyl ketone (MEK) | 3.3 | |
| Methylisobutyl ketone (MIBK) | 2.8 | |
| Methylisopropyl ketone (MIPK) | 2.8 | |
| Dimethyl ether | 1.3 | |

The polar organic solvent to be used in the process according to the invention has a dipole moment of more than 0.5D, preferably of more than 0.7D, more preferably of more than 1.0D. It is possible to change the relative amounts of monoperoxy ester and monoperoxy carbonate in the reaction mixture in view of the ketone peroxide and the acid halogen or halogen formate used by adjusting the polarity of the polar organic solvent.

In a suitable inert two-phase solvent system according to the invention, one of the solvents is an aqueous (alkali) phase and the other phase comprises as polar solvent for example alcohols, cycloalkanols, ethers, anhydrides, carbonates, alkylene glycols, amides, aldehydes, ketones, epoxides, esters, halogenated hydrocarbons such as chlorinated hydrocarbons, and mixtures thereof.

Specific examples of the above-mentioned polar solvents include, but are not limited to, diethyl ether, dimethyl ether, methylisobutyl ether, acetonitrile, ethyl acetate, methyl acetate, ethylene glycol, acetone, tetrahydrofuran, chloroform, methylene chloride, 1,2-dichloroethane, dimethyl carbonate, and the like.

By properly selecting the equivalent amount of acid halogen or halogen formate for use in the preparation process, the amounts of monoperoxy ester and monoperoxy carbonate can be adjusted further. Generally, the amount of acid halogen or halogen formate is in the range of 0.5–5 equivalents. In this case the amounts of monoperoxy ester and monoperoxy carbonate formed are at least 50% of the produced peroxides. Using 0.9–2 equivalents, the selectivity is increased further. Most preferred is an equivalent amount in the range of 0.9–1.5 equivalents. In that case the selectivity generally is above 60%, such as above 80% or even above 90%.

The proper selection of the ratio of acid halogen or halogen formate in the process also makes it possible to prepare asymmetrical peresters, percarbonates, or their mixed form by using a suitable amount of acid halogen or halogen formate in a second step to convert the remaining hydroperoxide groups. In all, one mole of the ketone peroxide (carrying two moles of hydroperoxide groups) will reacted with a total of two moles of acid halogen and/or halogen formate. By varying the amount of acylating agent in the first step and second step, the reactivity of the resulting mixture of product can be influenced. By reactivity is meant the rate at which the peroxide thermally decomposes at a certain temperature, such as conventionally determined by means of a differential scanning calorimeter (DSC) using chlorobenzene as a solvent.

Accordingly, it may be preferred to have residual T4-ketone peroxide in the final monoperester/monopercarbonate in order to make certain mixtures of peroxides, if so desired. This may be the case, for instance, when mixtures of symmetrical and asymmetrical diperoxy esters, diperoxy carbonates, or their mixed form are to be prepared. The advantage of such mixtures of symmetrical and asymmetrical diperoxy compounds again is that the reactivity of the resulting mixture can be varied by selecting the ratio of the various compounds in the mixture.

The reaction conditions are conventional. The temperature generally is in the range of −10 to 50° C. and suitably between 0–30° C. A practical range is from 5 to 15° C. Essentially the temperature is selected such that side reactions and decomposition of the materials are avoided.

The pH is basic, i.e. above 7. Generally, the pH is in the range of 9–14. In practice, the pH is above 10 and a practical range is from 11 to 13.5. One or more conventional base-type acylation catalysts are preferably used, such as hydroxides and tert-amines, including (substituted) pyridine, polyvinyl pyridine, and the like. The reaction proceeds under ambient pressure and in free contact with the atmosphere.

Suitable ketone peroxides to react with said acid halogen and halogen formate are those formed from the following ketones: acetone, acetophenone, methyl-n-amyl ketone, ethylbutyl ketone, ethylpropyl ketone, methylisoamyl ketone, methylheptyl ketone, methylhexyl ketone, ethylamyl ketone, dimethyl ketone, diethyl ketone, dipropyl ketone, methylethyl ketone, methylisobutyl ketone, methylisopropyl ketone, methylpropyl ketone, methyl-n-butyl ketone, methyl-t-butyl ketone, isobutyl heptyl ketone, diisobutyl ketone, methoxy acetone, cyclohexanone, 2,4,4-trimethyl cyclohexanone, N-butyl levulinate, ethyl acetoacetate, methylbenzyl ketone, phenyl ethyl ketone, methylchloromethyl ketone, methylbromomethyl ketone, and coupling products thereof; also other ketones having the appropriate $R_1$ and $R_2$ groups corresponding to the peroxides of formula II can be employed, as well as mixtures of two or more different ketones.

Preferred acid halogens comprise those wherein $R_3$ is a linear or branched $C_1$–$C_{12}$ alkyl, cycloalkyl, aryl, aralkyl, or alkaryl group, the aryl group preferably being a phenyl group. Typical examples are acid halogens obtainable from the following carbon acids: acetic acid, phenyl acetic acid, phenoxy acetic acid, propanoic acid, isobutyric acid, benzoic acid, 2-methyl benzoic acid, 2-methyl butanoic acid, 2-butenoic acid, 3-phenyl propenic acid, 2,2-dimethyl propanoic acid, 2,2-dimethyl butanoic acid, 2,2-dimethyl pentanoic acid, 2-ethyl butanoic acid, 3,5,5-trimethyl hexanoic acid, 2-ethyl hexanoic acid, neohexanoic acid, neoheptanoic acid, neodecanoic acid, octanoic acid, nonanoic acid, lauric acid, 3,5,5-trimethyl pentane dioic acid, hexane dioic acid, 3,5,5-trimethyl hexane dioic acid, 2,4,4-trimethyl hexane dioic acid, decane dioic acid, undecane dioic acid, dodecane dioic acid, cyclohexane carboxylic acid, 1,4-cyclohexane dicarboxylic acid, cyclohexane-1,4-diacetic acid, maleic acid, citric acid, 3-hydroxybutanoic acid, 4-hydroxybutanoic acid, 2-hydroxypentanoic acid, 3-hydroxypentanoic acid, 4-hydroxypentanoic acid, 5-hydroxypentanoic acid, hydroxyacetic acid, 2-hydroxyisobutyric acid, 2-hydroxypropanoic acid, 2-hydroxyhexanoic acid, hydroxypivalic acid, hydroxysuccinic acid, methyl succinic acid, citraconic acid, fumaric acid, oxalic acid, terephthalic acid, propenoic acid, and phthalic acid, and their corresponding methyl esters, ethyl esters, n-propyl esters, isopropyl esters, n-butyl esters, sec-butyl esters, isobutyl esters, ethylene glycol esters, and propylene glycol esters, as well as mixtures of these acid halogens.

Examples of the chloroformates used are:

2-(1-methylethoxy)phenyl chloroformate, 1-methylpropyl chloroformate, 4-methylphenyl chloroformate, 2,2,2-trichloro-1,1-dimethylethyl chloroformate, heptyl chloroformate, cyclohexyl methyl chloroformate, ethylene glycol bis(chloroformate), 3-(1,1-dimethylethyl)phenyl chloroformate, 3-(trichlorosilyl)propyl chloroformate, phenyl chloroformate, 3-methoxybutyl chloroformate, 2-phenoxyethyl chloroformate, 2,2-dimethyl-1,3-propane diol bis(chloroformate), phenyl methyl chloroformate, 9-octadecenyl chloroformate, 2-methylphenyl chloroformate, bisphenol A bis(chloroformate), 1,3-dimethyl butyl chloroformate, 3,4-dimethyl butyl chloroformate, 3,4-dimethyl phenyl chloroformate, trichloromethyl chloroformate, 1-chloroethyl chloroformate, chloromethyl chloroformate, 1,4-butane diol bis(chloroformate), 1,1-bis (ethoxycarbo)ethyl chloroformate, 3,5-dimethyl phenyl chloroformate, octyl chloroformate, ethyl chloroformate, octadecyl chloroformate, (2-oxo-1,3-dioxolan-4-yl)methyl chloroformate, 1,6-hexane diol bis(chloroformate), 2-chlorobutyl chloroformate, 4-methoxyphenyl chloroformate, 2-methylpropyl chloroformate, 2-(methylsulfonyl)ethyl chloroformate, dodecyl chloroformate, 1,4-cyclohexane dimethanol bis(chloroformate), 2-chloro-2-phenyl ethyl chloroformate, 2-acryloyloxyethyl chloroformate, 4-nitrophenyl chloroformate, n-butyl chloroformate, decyl chloroformate, 2-ethylhexyl chloroformate, 2-propenyl chloroformate, 2-chlorocyclohexyl chloroformate, 2-methyl-2-propenyl chloroformate, cyclohexyl chloroformate, 2-chloroethyl chloroformate, [4-(phenylazo)phenyl]methyl chloroformate, hexadecyl chloroformate, 1-naphthalenyl chloroformate, 2-[2-cyclopentyl-4-(1,1-dimethylethyl)phenoxy]-1-methylethyl chloroformate, 3,5,5-trimethyl hexyl chloroformate, isotridecyl chloroformate, tridecyl chloroformate, 4-(1,1-dimethylethyl)cyclohexyl chloroformate, 2,4,5-trichlorophenyl chloroformate, 3-chloropropyl chloroformate, tetradecyl chloroformate, 9H-fluoren-9-yl methyl chloroformate, (4-nitrophenyl)methyl chloroformate, methyl chloroformate, 2-(1-methylethyl)phenyl chloroformate, triethylene glycol bis(chloroformate), 2-methoxyethyl chloroformate, 1-methylethenyl chloroformate, 3-methylphenyl chloroformate, 2-bromoethyl chloroformate, diethylene glycol bis(chloro-formate), 3-methyl-5-(1-methylethyl)phenyl chloroformate, 2,2,2-tribromoethyl chloroformate, 2-ethoxyethyl chloroformate, 3-methyl-1,5-pentane diol bis(chloroformate), 4-methoxy carbophenyl chloroformate, ethenyl chloroformate, 1-methylethyl chloroformate, 2-(1-methylpropyl)phenyl chloroformate, 2,2,2-trichloroethyl chloroformate, pentyl chloroformate, cyclodecyl chloroformate, 4-(1,1-dimethylethyl)phenyl chloroformate, hexyl chloroformate, n-propyl chloroformate, 3-methoxy-3-methylbutyl chloroformate, 2-propoxyethyl chloroformate, 2-methoxy-1-methylethyl chloroformate, 2-butoxyethyl chloroformate, 2,2-dimethyl propyl chloroformate, 2,3-dihydro-2,2-dimethyl-7-benzofuranyl chloroformate, 1-chloroethyl chloroformate, cyclobutyl chloroformate, 5-methyl-2-(1-methylethyl)cyclohexyl chloroformate, 1,1-dimethyl ethyl chloroformate, 1-methylheptyl chloroformate, and mixtures of these chloroformates.

The preparation process according to the present invention may be supplemented such that diperoxy esters or diperoxy carbonates are formed. The reaction of the remaining hydroperoxide group in the monoperoxy ester and the monoperoxy carbonate can be carried out using conventional reaction conditions as used in the above process for the preparation of monoperoxy esters and monoperoxy carbonates (for instance: temperature 0–30° C., preferably 5–15° C.; and pH >10, preferably pH 11–13.5). Furthermore, use can be made of an inert two-phase solvent system comprising an apolar solvent. Apolar solvents are solvents having a dipole moment of less than 0.5D, in particular 0D.

Suitable apolar solvents generally are hydrocarbon solvents, aromatic hydrocarbon solvents, aralkyl solvents, paraffinic oils, white oils and silicone oils, as well as their mixtures. Useful hydrocarbon solvents include, but are not limited to, benzene, xylene, toluene, mesitylene, hexane, hydrogenated oligomers of alkanes such as Isopar$^R$ products (ex. Exxon), shellsol$^R$ products (ex Shell), pentane, hexane, heptane, decane, isododecane, decalin, toluene, xylene, mesitylene, benzene, and the like. Paraffinic oils useful as apolar solvents include, but are not limited to, halogenated paraffinic oils and paraffinic diesel oil. Other oils, including white oils, epoxidized soybean oils, and silicone oils are also useful in the present invention.

Asymmetrical diperoxy esters, diperoxy carbonates, and their mixed form, peroxy ester peroxy carbonate, having formula IV

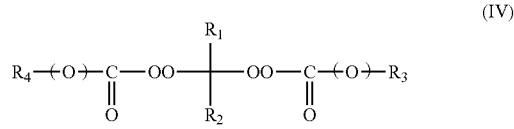

(IV)

wherein $R_4$ is selected from the same group as $R_3$, with the proviso that $R_3$ and $R_4$ do not have to same meaning, are formed when the respective acid halogens and/or halogen formates are different from those used in the preparation process as described for the monoperoxy ester and the monoperoxy carbonate.

The reaction conditions may be the same as for the preparation of the above symmetrical diperoxy esters and diperoxy carbonates.

In the formation of the mixed diperoxide having a formula V

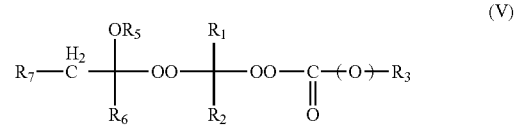

(V)

the reagent is an alkyl vinyl ether with the general formula VI

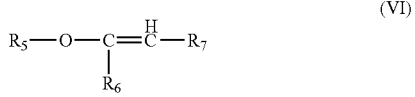

The groups $R_5$, $R_6$, and $R_7$ are independently selected from the group comprising $C_1$–$C_{20}$ alkyl, $C_3$–$C_{20}$ alkyl, $C_3$–$C_{20}$ cycloalkyl, $C_6$–$C_{20}$ aryl, $C_7$–$C_{20}$ aralkyl, and $C_7$–$C_{20}$ alkaryl, which groups may include linear or branched alkyl moieties; and each group $R_3$–$R_7$ may optionally be substituted with one or more groups selected from hydroxy, alkoxy, linear or branched alkyl, aryloxy, halogen, ester, carboxy, nitrile, and amido. $R_6$ and $R_7$ preferably are hydrogen.

Specific examples of the alkyl vinyl ether VI are: vinyl 2,2-bis(vinyloxymethyl)butyl ether, 2-methoxy-2-butene, allyl 2,3-epoxypropyl ether, n-propyl vinyl ether, 1-ethoxy-4-methyl-1-nonene, tertamyl vinyl ether, 2,2-bis (4-vinyloxyphenyl)propane, hexadecyl vinyl ether, methyl vinyl ether, 4-methylhexyl vinyl ether, 2-(2-ethoxyethoxy)ethyl vinyl ether, 2-methoxyethyl vinyl ether, 2-vinyloxy ethanol, 4-methyl-1-decenyl vinyl ether, benzyl 1-methyl vinyl ether, butane diol divinyl ether, tert.butyl vinyl ether, isobutyl vinyl ether, cyclohexane dimethanol divinyl ether, cyclohexyl vinyl ether, ethylene glycol divinyl ether, 1-ethoxy-4-(1-ethoxyvinyl)-3,3,5,5-tetramethyl cyclohexene, allyl vinyl ether, isopropyl vinyl ether, ethyl vinyl ether, tetraethylene glycol divinyl ether, 1,1,3-trimethoxypropene, 1-methoxy-1-buten-3-yne, heptyl vinyl ether, 4-(1-ethoxyvinyl)-3,3,5,5-tetramethyl cyclohexanone, 2-butoxyethyl vinyl ether, allyl ethyl ether, divinyl ether, 1,3-divinyloxy-2,2-dimethyl propane, 4-vinyloxybutanol, diethylene glycol divinyl ether, 4-(vinyloxymethyl) cyclohexyl methanol, isopentyl vinyl ether, diethylene glycol monovinyl ether, n-butyl vinyl ether, 1,4-bis(2-vinyloxyethyl)benzene, hexanediol divinyl ether, 1-methoxy-1,3-butadiene, decyl vinyl ether, 4-(allyloxymethyl)-1,3-dioxolan-2-one, 1,1-diethyl propyl vinyl ether, 2-methoxyvinyl benzene, octyl vinyl ether, bis(vinyloxy)methane, 1,4-dimethoxy-1,3-butadiene, 2,3-dimethoxy-1,3-butadiene, triethylene glycol divinyl ether, pentyl vinyl ether, octadecyl vinyl ether, 2-methoxypropene, triethylene glycol methyl vinyl ether, 2,3-epoxypropyl vinyl ether, dodecyl vinyl ether, 1,1-bis(vinyloxy)butane, hexyl vinyl ether, 6-vinyloxy hexanol, (z)-1-methoxy-1-buten-3-yne, phenyl vinyl ether, 2-ethylhexyl vinyl ether, poly-THF-divinyl ether, pluriol-E-200-divinyl ether, trimethylol propane trivinyl ether, aminopropyl vinyl ether, 2-diethyl aminoethyl vinyl ether, 2-ethoxy propene, 2-isobutoxy propene, 2-ethoxy-2-butene, 2-isobutoxy-2-propene, ethyl propenyl ether.

The alkyl vinyl ether addition reaction is carried out under conditions conventional for this type of addition reaction. The temperature generally is in the range of 0–30° C. and preferably 10–20° C. The reaction is carried out in the presence of an acid catalyst. The amount of catalyst generally is 1–30 g/mole, preferably 1–15 g/mole, of monoperoxy ester or monoperoxy carbonate.

The catalyst for the process is an acidic catalyst such as a $C_1$–$C_{10}$ alkane or aryl sulphonic acid, a halogenated $C_1$–$C_{10}$ alkane sulphonic acid, or a mixture of one or more of these compounds. The preferred catalysts for use are, but are not limited to, p-toluene sulfonic acid and methane sulfonic acid.

The peroxides according to the present invention produced according to the preparation processes according to the present invention may be used as initiators for polymer production and in particular for the preparation of poly(vinylchloride), (meth)acrylic polymers, polystyrene, polyethylene, and copolymers comprising vinyl chloride, (meth) acrylates, styrene and/or ethylene, but they are equally suitable for curing unsaturated polyester resins and for the modification of polymers (such as grafting of monomers onto the polymer, crosslinking, and/or degradation of the polymer).

In the present invention, the polymerization is conducted by any conventional process, except that a specified radical polymerization initiator (or composition) is used. The polymerization processes may be carried out in the usual manner, for example in bulk, suspension, emulsion, or solution. In the case of the production of ethylene (co)polymers according to the invention, the reaction usually is carried out under high pressure, e.g. about 1000 to about 3500 bar.

The amount of initiator, which varies depending on the polymerization temperature, the capacity for removing the heat of polymerization, and, where applicable, the kind of monomer to be used and the applied pressure, should be an effective amount for achieving polymerization. Usually, from 0.001–25% by weight of peroxide, based on the weight of the (co)polymer, is employed. Preferably, from 0.001–20% by weight of peroxide is employed and most preferably from 0.001–15% by weight.

The polymerization temperature for most reactions within the present invention usually is 30° to 350° C., preferably 40° to 300° C. In general, if it is below 30° C., the polymerization time becomes too long. However, when it exceeds 350° C., the radical is spent in the initial stage of the polymerization, making it difficult to attain a high conversion. In order to reduce the amount of unreacted monomer, however, it is also possible to conduct the polymerization using a temperature profile, e.g., to perform the initial polymerization at below 100° C. and then elevate the temperature above 100° C. to complete the polymerization. These variations are all known to the man skilled in the art, who will have no difficulty selecting the reaction conditions of choice, depending on the particular polymerization process and the specific radical polymerization initiator to be used.

Suitable monomers for polymerization using the ketone peroxides according to the present invention are olefinic or ethylenically unsaturated monomers, for example substituted or unsubstituted vinyl aromatic monomers, including styrene, α-methyl styrene, p-methyl styrene, and halogenated styrenes; divinyl benzene; ethylene; ethylenically unsaturated carboxylic acids and derivatives thereof, such as (meth)acrylic acids, (meth)acrylic esters, such as 2-ethylhexyl acrylate, 2-ethylhexyl methacrylate, and glycidyl methacrylate; ethylenically unsaturated nitriles and amides, such as acrylonitrile, methacrylonitrile, and acrylamide; substituted or unsubstituted ethylenically unsaturated monomers, such as butadiene, isoprene, and chloroprene; vinyl esters, such as vinyl acetate and vinyl propionate; ethylenically unsaturated dicarboxylic acids and their derivatives including mono- and diesters, anhydrides, and imides, such as maleic anhydride, citraconic anhydride, citraconic acid, itaconic acid, nadic anhydride, maleic acid, fumaric acid, aryl, alkyl, and aralkyl citraconimides and maleimides; vinyl halides, such as vinyl chloride and vinylidene chloride; vinyl ethers, such as methyl vinyl ether and n-butyl vinyl ether; olefins, such as isobutene and 4-methyl pentene; allyl compounds, such as (di)allyl esters, for example diallyl phthalates, (di)allyl carbonates, and triallyl (iso)cyanurate.

During (co)polymerization, the formulations may also contain the usual additives and fillers. As examples of such additives may be mentioned: stabilizers such as inhibitors of oxidative, thermal, or ultraviolet degradation, lubricants, extender oils, pH controlling substances, such as calcium carbonate, release agents, colourants, reinforcing or non-reinforcing fillers such as silica, clay, chalk, carbon black, and fibrous materials, such as glass fibres, plasticizers, diluents, chain transfer agents, accelerators, and other types of peroxides. These additives may be employed in the usual amounts.

Finally, the polymerization process of the present invention can be employed to introduce functional groups into the (co)polymers produced therewith. This may be accomplished by employing a peroxide which contains one or more functional groups attached thereto. These functional groups remain intact in the free radicals formed by the ketone peroxides and thus are introduced into the (co) polymer. Conventional polymerization conditions and equipment may be used to achieve this object of the present invention.

The peroxides according to the invention may be used as a curing agent for unsaturated polyesters and unsaturated polyester resins. Such resins usually include an unsaturated polyester and one or more ethylenically unsaturated monomers. Suitable polymerizable monomers include styrene, α-methyl styrene, p-methyl styrene, chlorostyrenes, bromostyrenes, vinyl benzyl chloride, divinyl benzene, diallyl maleate, dibutyl fumarate, triallyl phosphate, triallyl cyanurate, diallyl phthalate, diallyl fumarate, methyl(meth)acrylate, n-butyl(meth)acrylate, ethyl acrylate, and mixtures thereof which are copolymerizable with the unsaturated polyesters. The unsaturated polyesters are, for example, polyesters as obtained by esterifying at least one ethylenically unsaturated di- or polycarboxylic acid, anhydride or acid halide, such as maleic acid, fumaric acid, glutaconic acid, itaconic acid, mesaconic acid, citraconic acid, allylmalonic acid, tetrahydrophthalic acid, and others, with saturated and unsaturated di- or polyols, such as ethylene glycol, diethylene glycol, triethylene glycol, 1,2- and 1,3-propane diols, 1,2-, 1,3-, and 1,4-butane diols, 2,2-dimethyl-1,3-propane diols, 2-hydroxymethyl-2-methyl-1,3-propane diol, 2-buten-1,4-diol, 2-butyn-1,4-diol, 2,4,4-trimethyl-1,3-pentane diol, glycerol, pentaerythritol, mannitol, and others. The di- or polycarboxylic acids may be partially replaced by saturated di- or polycarboxylic acids, such as adipic acid, succinic acid, and others and/or by aromatic di- or polycarboxylic acids, such as phthalic acid, trimellitic acid, pyromellitic acid, isophthalic acid, and terephthalic acid. The acids used may be substituted with groups such as halogen. Suitable halogenated acids include tetrachlorophthalic acid and tetrabromophthalic acid.

The peroxides of the present invention are suitable for use in the modification of polymers. More particularly, these peroxides can be employed in processes for grafting monomers onto polymers such as polyethers, polyolefins, and elastomers, and for the functionalization of polyolefins in the case of functional group-containing ketone peroxides of the present invention. In general, the peroxide may be brought into contact with the (co)polymer in various ways, depending upon the particular object of the modification process. For example, if surface modification of a three-dimensional polymeric object is desired, the ketone peroxide may be applied to the surface of the material to be modified. Alternatively, if it is desired to modify the (co)polymer homogeneously throughout the (co)polymeric matrix, then the peroxide may be mixed with the material to be modified, which material may be in the molten state, in the form of a solution, or, in the case of an elastomer, in a plastic state. It is also possible to mix the (co)polymer when in the powder or the granular form with the ketone peroxide.

The peroxides are also suitable as an agent for the modification of polymers, such as polyethylene, polypropylene, polybutadiene, and copolymers of two or more olefins. Modification includes crosslinking, degradation, and grafting of monomers. Polymers may be in the liquid form, e.g., liquid rubbers. In general, any (co)polymer comprising abstractable hydrogen atoms, in particular polyolefins, can be modified by the present process. The (co)polymeric material treated by the process of the present invention may take any physical form including finely divided particles (flakes), pellets, film, sheet, in the melt, in solution, and the like. In the preferred embodiments of the present invention the (co)polymeric material is in the particulate form suitable for powder modification in a substantially oxygen-free atmosphere, in the melt form suitable for modification in an air-containing atmosphere or a nitrogen atmosphere, or in solution in a suitable solvent.

The amount of peroxide used in the modification process of the present invention should be an effective amount for achieving significant modification of the (co)polymer when treating a (co)polymer. More particularly, from 0.001–15.0% by weight of peroxide, based on the weight of the (co)polymer, should be employed. More preferably, from 0.005–10.0% by weight is employed. Most preferably, an amount of 0.01–5.0% by weight is employed.

It is noted that in the preparation processes the ketone peroxide may be pure T4 peroxide (as shown in general formula II) or may comprise 5%–30%, such as 25%–25% and 10%–15%, of the corresponding T3 peroxide having the general formula II':

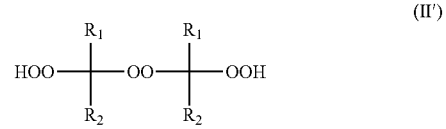

(II')

wherein $R_1$ and $R_2$ have the identified meaning. The presence of the corresponding T3 peroxide has no effect on its use as polymerization initiator, curing agent, and modifying agent.

The peroxides can be prepared, transported, stored, and applied in the form of powders, granules, pellets, pastilles, flakes, slabs, pastes, solid masterbatches, and liquids. These formulations may have the form of a dispersion, such as a suspension or an emulsion. The formulations may be phlegmatized if necessary, depending on the particular peroxide and its concentration in the formulation. Which of these forms is preferred depends partly on the application for which it will be used and partly on the manner in which it will be mixed. Also, considerations of safety may play a role to the extent that phlegmatizers may have to be incorporated into certain compositions to ensure their safe handling.

The formulations of the present invention are transportable, storage stable, and contain 1.0–90% by weight of one or more peroxides according to the present invention. Transportable means that the formulations of the present invention have passed the pressure vessel test (PVT). Storage stable means that the formulations of the present invention are both chemically and physically stable during a reasonable storage period under standard conditions.

More preferred formulations in accordance with the present invention contain 10–75% by weight of one or more of the ketone peroxides, most preferably these formulations contain 20–60% by weight of the ketone peroxides.

The formulations of the present invention can be liquids, solids, or pastes, depending on the melting point of the peroxide and the diluent employed. Liquid formulations can be made using liquid phlegmatizers for the ketone peroxide, liquid plasticizers, organic peroxides, and mixtures thereof as the diluent. The liquid component generally is present in an amount of 1–99% by weight of the composition. Preferably, 10–90% by weight, more preferably 30–90% by weight, and most preferably 40–80% by weight of the liquid formulation consists of liquid diluents.

It should be noted that certain phlegmatizers may not be suitable for use with all of the ketone peroxides of the present invention. More particularly, in order to obtain a safe composition, the phlegmatizer should have a certain minimum flash point and a boiling point relative to the decomposition temperature of the ketone peroxide such that the phlegmatizer cannot be boiled off leaving a concentrated, unsafe ketone peroxide composition behind. Thus, the lower-boiling phlegmatizers mentioned below may only be useful, for example, with particular substituted ketone peroxides of the present invention which have a low decomposition temperature.

In liquid formulations a liquid carrier or diluent is used. Preferably, this carrier or diluent is a solvent. For the monoperoxy esters and monoperoxy carbonates according to the present invention, both polar and apolar solvents may be used. For the diperoxy esters, diperoxy carbonates, and mixed diperoxides only apolar solvents are used. Examples of both polar and apolar solvents are those given for the preparation of the various ketone peroxides.

In the solid and/or paste formulations of the present invention solid carrier materials are employed. Examples of such solid carriers are low-melting solids, such as dicyclohexyl phthalate, dimethyl fumarate, dimethyl isophthalate, triphenyl phosphate, glyceryl tribenzoate, trimethylol ethane tribenzoate, dicyclohexyl terephthalate, paraffinic waxes, dicyclohexyl isophthalate; polymers and inorganic supports. Inorganic supports include materials such as fumed silica, precipitated silica, hydrophobic silica, chalk, whiting, surface-treated clays such as silane-treated clays, calcined clays, and talc.

Polymers useful in the formulations of the present invention include polyethylene, polypropylene, ethylene/propylene copolymers, ethylene/ propylene/diene monomer terpolymers, chlorosulphonated polyethylene, chlorinated polyethylene, polybutylene, polyisobutylene, ethylene/vinyl acetate copolymers, polyisoprene, polybutadiene, butadiene/styrene copolymers, natural rubber, polyacrylate rubber, butadiene/acrylonitrile copolymers, acrylonitrile/butadiene/styrene terpolymers, silicone rubber, polyurethanes, polysulphides, solid paraffins, and polycaprolactone.

Storage stable formulations must be both physically and chemically stable. By physically stable formulations are meant those formulations which do not suffer from significant phase separation upon storage. The physical stability of the present formulations can, in some instances, be improved by the addition of one or more thixotropic agents selected from cellulose esters, hydrogenated castor oil, and fumed silica. Examples of such cellulose esters are the reaction products of cellulose and acid compounds selected from, for example, acetic acid, propionic acid, butyric acid, phthalic acid, trimellitic acid, and mixtures thereof.

By chemically stable formulations are meant those formulations which do not lose a significant amount of their active oxygen content upon storage. The chemical stability of the present formulations can, in some instances, be improved by the addition of one or more known additives including sequestering agents such as dipicolinic acid and/or antioxidants such as 2,6-di(t-butyl)-4-methyl phenol and para-nonyl phenol.

The formulations of the present invention may also contain optional other additives, as long as these do not have any significant adverse effect on the transportability and/or storage stability of the formulations. As examples of such additives may be mentioned: anti-caking agents, free-flowing agents, anti-ozonants, anti-oxidants, anti-degradants, U.V. stabilizers, coagents, fungicides, antistats, pigments, dyes, coupling agents, dispersing aids, blowing agents, lubricants, process oils, and mould-release agents. These additives may be employed in their usual amounts.

The ketone peroxides according to the invention may also be used as a dispersion, preferably in a polar medium. The medium in which the initiator according to the invention is dispersed should be inert towards the initiator and so polar that the initiator will hardly dissolve in it. The initiator preferably is dispersed in water, an alcohol, or mixtures thereof. Most preferable is a dispersion in water. The use of such a medium makes for comparatively easy removal of any remnant, for example after the modification of the (co)polymer, if so desired. Furthermore, the use of water or alcohols is attended with far fewer organoleptic and other drawbacks than the use of organic diluents, such as toluene and xylene, which has been common up to now.

As is well-known to the skilled person, the use of other adjuvants in initiator dispersions may be advisable or even essential in order to ensure the dispersion's chemical and/or physical stability for a sufficiently long period of time. For instance, if the storage temperature of the initiator dispersion is lower than the freezing point of the medium in which the initiator is dispersed, an appropriate freezing point depression agent can be added to counteract freezing. Also, a wide range of substances can be used for altering the rheology of the formulation. To this end generally use is made of one or more surface-active materials and one or more thickeners. If so desired, other additives may be incorporated into the formulation. As examples of such additives may be mentioned pH buffers, biocides, chemical stabilizers which counteract premature decomposition of the initiator, and anti-agers which counteract the particle size growth in the dispersion.

The following examples illustrate the preparation processes for the monoperoxy ester, monoperoxy carbonate, diperoxy esters, and diperoxy carbonate and mixed peroxides according to the present invention and their applications.

EXAMPLE 1

Preparation of 1-hydroperoxy-1,3-dimethyl butyl peroxy-2-ethyl hexanoate

In to a 200 ml beaker were charged 50 g of methylisobutyl ketone peroxide in diethyl ether (containing 0.1051 mole T4 and 0.0016 mole T3), 25 g of decane, 10 g of NaCl-25%, and 20 g of demi-water. The pH was adjusted with KOH-45% to 13.5 at a temperature of 8–12° C. Then 17.4 g (0.107 mole;

1 eq.) of 2-ethylhexanoyl chloride were dosed in 25 minutes simultaneously with the lye, with the pH kept at >13.5. The mixture was stirred for another 60 minutes at 5–8° C.

After separation of the water layer, the organic layer was washed with NaOH-4N and NaHCO$_3$-6%. The product was dried over magnesium sulphate and evaporated. Yield: 57.6 g of product with an active oxygen content of 5.02% (chemical yield: 85%).

Ratio mono:bis=80:20.

EXAMPLE 2

Preparation of 1-hydroperoxy-1,3-dimethyl butyl peroxy-2-ethyl hexanoate

As in Example 1, but with a ratio of 2.1 moles of 2-ethylhexanoyl chloride to 1 mole of methylisobutyl ketone peroxide in diethyl ether, isododecane being used as a co-solvent. Here the product also was the monoperoxyester. Ratio mono:bis=90:10.

EXAMPLE 3

Preparation of 1-hydroperoxy-1,3-dimethyl butyl peroxy-2-ethyl hexanoate

As in Example 1, but with a ratio of 5 moles of 2-ethylhexanoyl chloride to 1 mole of methylisobutyl ketone peroxide in diethyl ether, no extra co-solvent being added. Here the product was a mixture of monoperoxyester and bisperoxyester. Ratio mono:bis=50:50.

EXAMPLE 4

(Not According to the Invention) Preparation of 2,2-bis(2-ethylhexanoylperoxy)-4-methyl pentane Into a 200 ml beaker were charged 12 g of methylisobutyl ketone peroxide in water (containing 0.0533 mole T4 and 0.0008 mole T3), 25 g of petroleum ether (boiling range 40–60° C.), 12.5 g of NaCl-25%, and 10 g of demi-water. The pH was adjusted with KOH45% to 13.5 at a temperature of 5–8° C. Then 19.1 g (0.117 mole; 2.2 eq.) of 2-ethylhexanoyl chloride were dosed in 25 minutes simultaneously with the lye, with the pH kept at >13.5. The mixture was stirred for another 90 minutes at 2–4° C. After separation of the water, layer 25 g of isododecane were added, and the organic layer was washed with NaOH-4N and NaHCO$_3$-6%. The product was dried over magnesium sulphate and evaporated. Yield: 42.3 g of product with an active oxygen content of 3.22% (chemical yield:80%).

Ratio mono:bis=20:80.

EXAMPLE 5

Preparation of 1-hydroperoxy-1,3-dimethyl butyl peroxypivalate

Into a 200 ml beaker were charged 50 g of methylisobutyl ketone peroxide in diethyl ether (containing 0.1051 mole T4 and 0.0016 mole T3), 25 g of decane, 10 g of NaCl-25%, and 20 g of demi-water. The pH was adjusted with KOH-45% to 13.5 at a temperature of 8–12° C. Then 12.9 g (0.107 mole; 1 eq.) of pivaloyl chloride were dosed in 25 minutes simultaneously with the lye, with the pH kept at >13.5. The mixture was stirred for another 45 minutes at 3–5° C. After separation of the water layer, the organic layer was washed with NaOH-4N and NaHCO$_3$-6%. The product was dried over magnesium sulphate and evaporated. Yield: 43.9 g of product with an active oxygen content of 4.60% (chemical yield:59%).

Ratio mono:bis=80:20.

EXAMPLE 6

Preparation of 1-hydroperoxy-1,2-dimethyl propyl peroxy-2-ethyl hexanoate

Into a 200 ml beaker were charged 43.1 g (0.07 mole) of methylisopropyl ketone peroxide in butyl acetate, 15 g of decane, and 10 g of NaCl-25%. The pH was adjusted with KOH-45% to 13.5 at a temperature of 8–12° C. Then 22.8 g (0.14 mole; 2 eq.) of 2-ethylhexanoyl chloride were dosed in 25 minutes simultaneously with the lye, with the pH kept at >13.5. The mixture was stirred for another 60 minutes at 4–6° C. After separation of the water layer, the organic layer was washed with NaOH-4N and NaHCO$_3$-6%. The product was dried over magnesium sulphate and evaporated. Yield: 31.8 g of product with an active oxygen content of 5.61% (chemical yield: 80%).

Ratio mono:bis=60:40.

EXAMPLE 7

Preparation of 1-hydroperoxy-1.3-dimethyl butyl peroxy-2-ethylhexyl carbonate

Into a 200 ml beaker were charged 25 g of methylisobutyl ketone peroxide in diethyl ether (containing 0.0567 mole T4 and 0.0008 mole T3) and 5 g of pyridine at a temperature of 0–5° C. Then 10.9 g (0.0567 mole; 1 eq.) of 2-ethylhexyl chloroformate were dosed in 10 minutes at 0–4° C. The mixture was stirred for another 90 minutes at 0–2° C. After separation of the water layer, the organic layer was washed with HCl-1N and NaHCO$_3$-6%. The product was diluted with 10 g isododecane, dried over magnesium sulphate, and evaporated. Yield: 27.2 g of product with an active oxygen content of 6.08% (chemical yield:90%).

Ratio mono:bis=80:20.

EXAMPLE 8

Preparation of 2,2-bis(2-ethylhexanoylperoxy)-4-methyl pentane

Into a 200 ml beaker were charged 50 g of 1-hydroperoxy-1,3-dimethyl butyl peroxy-2-ethyl hexanoate (0.06 mole) in n-decane, 10 g of NaCl-25%, and 20 g of demi-water. The pH was adjusted with KOH-45% to 13.5 at a temperature of 8–12° C. Then 9.8 g of 2-ethylhexanoyl chloride were dosed in 20 minutes simultaneously with the lye, with the pH kept at >13.5. The mixture was stirred for another 60 minutes at 5–8° C. After separation of the water layer, the remaining hydroperoxide was reduced with a sulphite reduction. The organic layer was washed with NaHCO$_3$-6%. The product was dried over magnesium sulphate.

Yield: 47.4 g of product with an active oxygen content of 3.77% (chemical yield:93%).

Ratio mono:bis=1:99.

With the same result a mixture of 1-hydroperoxy-1,3-dimethyl butylperoxy-2-ethyl hexanoate containing 5–10% 1-(2-ethylhexanoylperoxy)-1,3-dimethyl butylperoxy-1,3-dimethylbutyl hydroperoxide was converted to the bisperoxyester.

EXAMPLE 8a

Preparation of 2,2-bis(2,2-dimethylpropanoylperoxy)-4-methyl pentane

Into a 200 ml beaker were charged 46.6 g of 1-hydroperoxy-1,3-dimethyl butyl pivalate in isododecane and 25 g of NaCl-25%. The pH was adjusted with KOH45% to 13.5 at a temperature of 8–12° C. Then 3.5 g of pivaloyl chloride were dosed in 20 minutes simultaneously with the lye, with the pH kept at >13.5. The mixture was stirred for another 140 minutes at 5–8° C. After separation of the water layer, the remaining hydroperoxide was reduced with a sulphite reduction. The organic layer was washed with $NaHCO_3$-6%. The product was dried over magnesium sulphate. Yield: 38.1 g of product with an active oxygen content of 3.33% (chemical yield:90%).

Ratio mono:bis=1:99.

EXAMPLE 8b

Preparation of bis(1-acetylperoxy)-1,2-dimethyl propane

Into a 200 ml beaker were charged 43.1 g (0.07 mole) of methylisopropyl ketone peroxide in butylacetate, 15 g of isododecane, and 10 g of NaCl-25%. The pH was adjusted with KOH45% to 13.5 at a temperature of 8–12° C. Then 11 g (0.14 mole; 2 eq.) of acetyl chloride were dosed in 25 minutes simultaneously with the lye, with the pH kept at >13.5. The mixture was stirred for another 60 minutes at 4–6° C. After separation of the water layer, the organic layer was washed with NaOH-4N and $NaHCO_3$-6%. The product was dried over magnesium sulphate and evaporated. To this mono-adduct isododecane was added, as well as 25 g of NaCl-25%. The pH was adjusted with KOH45% to 13.5 at a temperature of 8–12° C. Then 7.8 g of acetyl chloride were dosed in 20 minutes simultaneously with the lye, with the pH kept at >13.5. The mixture was stirred for another 60 minutes at 5–8° C. After separation of the water layer, the remaining hydroperoxide was reduced with a sulphite reduction. The organic layer was washed with $NaHCO_3$-6%. The product was dried over magnesium sulphate. Chemical yield: 90%, ratio mono:bis=1:99.

EXAMPLE 9

Preparation of 1-(2-ethylhexanoylperoxy)-1,3-dimethyl butyl-peroxy pivalate

Into a 50 ml beaker were charged 15 g of 1-hydroperoxy-1,3-dimethyl butyl-peroxy-2-ethyl hexanoate (0.0169 mole) in isododecane and 7.5 g of NaCl-25%. The pH was adjusted with KOH-45% to 13.5 at a temperature of 5–8° C. Then 3.1 g of pivaloyl chloride were dosed in 20 minutes simultaneously with the lye, with the pH kept at >13.5. The mixture was stirred for another 60 minutes at 5–8° C. After separation of the water layer, the remaining hydroperoxide was reduced with a sulphite reduction. The organic layer was washed with $NaHCO_3$-6%. The product was dried over magnesium sulphate.

Yield: 13.2 g of product with an active oxygen content of 3.93% (chemical yield:96%).

Ratio mono:bis=1:99.

EXAMPLE 9a

Preparation of 1-(2-ethylhexanoylperoxy)-1,3-dimethyl butyl-peroxy pivalate (ratio 1/1)

Into a 200 ml beaker were charged 50 g of methylisobutyl ketone peroxide (0.1051 mole T4 and 0.0016 mole T3) in diethyl ether and 15 g of NaCl-25%. The pH was adjusted with NaOH-25% to 9.5 at a temperature of 5° C. Then 12.9 g (1 equivalent) of pivaloyl chloride were dosed in 25 minutes simultaneously with the lye, with the pH kept at >9.5. The mixture was stirred for another 20 minutes at 5° C. After separation of the water layer, 25 g of isododecane were added and the organic layer was washed with NaOH-4N and $NaHCO_3$-6%. The product was dried over magnesium sulphate and the residual diethyl ether evaporated.

Yield: 50 g of intermediate, being 1-hydroxy-1,3-dimethyl butylperoxy pivalate (0.107 mole) in isododecane.

Into a 200 ml beaker were charged 50 g of the intermediate and 15 g of NaCl-25%. The pH was adjusted with NaOH-25% to 11.5 at a temperature of 5° C. Then 17.3 g (1 equivalent) of 2-ethylhexanoyl chloride were dosed in 45 minutes simultaneously with the lye, with the pH kept at >11.5. The mixture was stirred for another 60 minutes at 5° C. After separation of the water layer, the remaining hydroperoxide was reduced with a sulphite reduction. The organic layer was washed with $NaHCO_3$-6%. The product was dried over magnesium sulphate.

Yield: 69 g of product (0.102 mole) with an active oxygen content of 4.72% (chemical yield:95%). One hour half-life temperature 43° C.

EXAMPLE 9b

Preparation of 1-(2-ethylhexanoylperoxy)-1,3-dimethyl butylperoxy pivalate (Ratio 0.8 eq. Pivaloyl chloride/1.2 eq. 2-ethylhexanoyl chloride)

Into a 200 ml beaker were charged 50 g of methylisobutyl ketone peroxide (0.1051 mole T4 and 0.0016 mole T3) in diethyl ether and 15 g of NaCl-25%. The pH was adjusted with NaOH-25% to 9.5 at a temperature of 5° C. Then 10.3 g (0.8 equivalent) of pivaloyl chloride were dosed in 25 minutes simultaneously with the lye, with the pH kept at >9.5. The mixture was stirred for another 20 minutes at 5° C. After separation of the water layer, 25 g of isododecane were added and the organic layer was washed with NaOH-4N and $NaHCO_3$-6%. The product was dried over magnesium sulphate and the residual diethyl ether evaporated.

Yield: 48 g of intermediate, being 1-hydroxy-1,3-dimethyl butylperoxy pivalate (0.086 mole) in isododecane.

Into a 200 ml beaker were charged 48 g of the intermediate and 15 g of NaCl-25%. The pH was adjusted with NaOH-25% to 11.5 at a temperature of 5° C. Then 20.8 g (1.2 equivalent) of 2-ethylhexanoyl chloride were dosed in 45 minutes simultaneously with the lye, with the pH kept at >11.5. The mixture was stirred for another 60 minutes at 5° C. After separation of the water layer, the remaining hydroperoxide was reduced with a sulphite reduction. The organic layer was washed with $NaHCO_3$-6%. The product was dried over magnesium sulphate.

Yield: 70 g of product (0.100 mole) with an active oxygen content of 4.57% (chemical yield:93%). One hour half-life temperature 46° C.

EXAMPLE 10

Preparation of 1-(1-isobutoxyethyl-peroxy)-1,3-dimethyl butylperoxy pivalate Into a 50 ml beaker were charged 15 g 1-hydroperoxy-1,3-dimethyl butylperoxy pivalate (0.0166 mole) in isododecane and 0.15 g p-toluene sulphonic acid monohydrate at a temperature of 10° C. Then 1.7 g isobutyl vinyl ether were dosed in 2 minutes, with the temperature being kept at 10° C. by cooling with an ice water bath. The mixture was stirred for another 10 minutes at 10° C., washed with $NaHCO_3$-6%, and dried over magnesium sulphate.

Yield: 13.5 g of product with an active oxygen content of 3.22% (chemical yield:82%).

Ratio mono:bis=1:99.

EXAMPLE 11

Preparation of 13,26-diisobutyl-13,26-dimethyl-1,2,4,9,11,12,14,15,17,22,24,25-dodecaoxa-3,10,16,23-tetraoxycyclohexacosane Into a 200 ml beaker were charged 30 g of methylisobutyl ketone peroxide (0.0710 mole T4 and 0.0012 mole T3) in diethyl ether/isododecane and 12.5 g of NaCl-25%. The pH was adjusted with NaOH-25% to 9.5 at a temperature of 5° C. Then 15.3 g (0.0712 mole) of 1,4-butane diol bischloroformate were dosed in 25 minutes simultaneously with the lye, with the pH kept at >9.5. The mixture was stirred for another 60 minutes at 5° C. After separation of the water layer, the organic layer was washed with $NaHCO_3$-6%. The product was dried over magnesium sulphate and the residual diethyl ether evaporated.

Yield: 33 g of intermediate in isododecane.

Into a 200 ml beaker were charged 33 g of the intermediate and 25 g of NaCl-25%. The pH was adjusted with NaOH-25% to 11.5 at a temperature of 5° C. The mixture was stirred for another 60 minutes at 5° C. to obtain the cyclic bis-adduct. After separation of the water layer, the remaining hydroperoxide was reduced with a sulphite reduction. The organic layer was washed with $NaHCO_3$-6%. The product was dried over magnesium sulphate.

Yield: 19 g of product with an active oxygen content of 4.98% (chemical yield: 20%).

EXAMPLE 12

Polymerization of Vinyl Chloride

Peroxyesters of the present invention with 1-hour half-life temperatures in the range of 40°–60° C. were evaluated in vinyl chloride polymerization with good results. The polyvinyl chloride was produced according to an experimental procedure to be used for the 5-litre autoclave, with the conversion being measured in time via the "butane tracer technique" (ref.: T. Y. Xie, A. E. Hamielek, P. E. Wood, O. R. Woods and H. Westmijze, *J. Appl. Pol. Sci.*, Vol. 41 (1990)). A 5-litre stainless steel reaction vessel equipped with: 1 baffle, a three-bladed stirrer, (n=450 rpm), a pressure transducer, a nitrogen purge, and the sampling device for the butane tracer technique was charged with 2700 g demineralized water and 0.15% Gohsenol KP-08 (1.0125 g) on vinyl chloride, and with a buffer: 1 g $Na_2HPO_4$ ex Baker, No. 0303+1 g $Na_2HPO_4$ ex Baker No. 0306. The vessel was closed and pressurized with 15 bar nitrogen. The vessel was evacuated and pressurized with nitrogen (5 bar) at least three times. Subsequently the vessel was fed with the peroxy ester of the present invention identified in Table 1 as an initiator. The vessel was evacuated again and subsequently charged with vinyl chloride. The temperature was increased from ambient to the polymerization temperature (37–62° C.) in about 30 minutes (37 and 42° C.), up to 60 minutes for the higher temperature (53/57/62° C.). After 10 minutes of polymerization time, polyvinyl alcohol was fed from a nitrogen pressurized bomb. The standard polymerization time was 8 hours. Atmospheric pressure was attained before the vessel was opened, and the vessel was evacuated for at least half an hour. The polyvinyl chloride formed was filtered and washed on a glass filter (S2). Subsequently, the polyvinyl chloride was dried in a fluid bed dryer at 60° C.

The results are shown in Table 2.

TABLE 2 vinyl chloride polymerization with ketone peroxides at different temperatures.

| Type of peroxide | Temp ° C. | perox % | yield % | CPT min |
|---|---|---|---|---|
| 2,2 bis (2,2dimethylpropanoyl-peroxy)-4-methyl pentane (Example 8a) | 37 | 0.12 | 87.7 | 197 |
| 2,2 bis (2,2dimethylpropanoyl-peroxy)-4-methyl pentane (Example 8a) | 42 | 0.12 | 88.9 | 175 |
| 2,2 bis (2,2dimethylpropanoyl-peroxy)-4-methyl pentane (Example 8a) | 48 | 0.10 | 87.3 | 197 |
| 2,2 bis (2,2dimethylpropanoyl-peroxy)-4-methyl pentane (Example 8a) | 53 | 0.12 | 92 | 300 |
| 2,2 bis(2-ethylhexanoylperoxy)-4-methyl pentane (Example 8) | 57 | 0.05 | 75 | 400 |
| 2,2 bis(2-ethylhexanoylperoxy)-4-methyl pentane (Example 8) | 57 | 0.075 | 90.7 | 148 |
| 2,2 bis(2-ethylhexanoylperoxy)-4-methyl pentane (Example 8) | 57 | 0.1 | 93.1 | 117 |
| 2,2 bis(2-ethylhexanoylperoxy)-4-methyl pentane (Example 8) | 57 | 0.1 | 92.4 | 120 |
| 2,2 bis(2-ethylhexanoylperoxy)-4-methyl pentane (Example 8) | 62 | 0.05 | 68 | 480 |
| 1-(2-ethylhexanoylperoxy)-1,3-dimethyl butylperoxy pivalate (Example 9) | 42 | 0.12 | 89.2 | 208 |
| 1-(2-ethylhexanoylperoxy)-1,3-dimethyl butylperoxy pivalate (Example 9) | 57 | 0.1 | 87.4 | 164 |

% peroxy = mass % on VCM
CPT = constant pressure time: time until vinyl chloride pressure drop (about 75% conversion)

EXAMPLE 13

Polymerization of Styrene

Bis(1-acetylperoxy)-1,2-dimethyl propane (Example 8b) was used as initiator to polymerize styrene in a mass polymerization process. Tests were performed in closed ampoules. Polystyrene with a high molecular weight was obtained.

Mass polymerizations were carried out in 3 ml glass ampoules placed in a heated oil bath. Styrene (distilled, ex Merck) was polymerized at 90° C. The initiator was a ketone peroxide of the present invention and was present in a concentration of 0.38 meq./100 g styrene. Samples were taken at different times. The ampoules were removed from the oil bath and quenched in a 20 ml solution of dichloromethane containing n-butyl benzene and Topanol® OC.

The weight-average (Mw) and number-average (Mn) molecular weights were determined by means of gel permeation chromatography (Water gel permeation chromatograph, column "PL gel 5 microns mixed C" 300×7.5 mm ex Polymer Laboratories, eluent THF, 1 ml/min, temperature: 40° C., Waters 410 differential refractometer reference PS polymer standards ex Polymer Laboratories). The dispersity was calculated as (Mw/Mn). The results are shown in Table 3.

TABLE 3

Polymerization of styrene using bis(1-acetylperoxy)-1,2-dimethyl propane

| Polymerization time (h) | Mw (×10−3) (Dalton) | Mn (×10−3) (Dalton) | Dispersity |
|---|---|---|---|
| 4 | 235 | 92 | 2.6 |
| 5 | 256 | 97 | 2.6 |
| 6 | 281 | 102 | 2.8 |
| 7 | 304 | 104 | 2.9 |
| 8 | 310 | 105 | 2.9 |

EXAMPLE 14

The performance of 2,2-bis(2-ethylhexanoylperoxy)-4-methyl pentane (Example 8) as curing agent for unsaturated polyester was compared with that of Trigonox 21 (t-butyl peroxy-2-ethyl hexanoate).

The time-temperature curve was measured at 100° C. on compounds containing 100 parts of polyester resin, 150 parts of sand as filler, and 1 part of peroxide. The method followed was as outlined by the Society of Plastic Institute. 25 g of compound were poured into a test tube and a thermocouple was mounted through the enclosure cork in the middle of the tube. The glass tube was then placed in oil bath maintained at a specific test temperature, and the time-temperature curve was measured. From the curve the following parameters were calculated:

Gel time (GT)=time in minutes elapsed between 16.7° C. below and 5.6° C. above the bath temperature.

Time to peak exotherm (TTP)=time elapsed between the start of the experiment and the moment the peak temperature is reached.

Peak exotherm (PE)=the maximum temperature reached.

Results:

| Compound | Test temp. (° C.) | GT (minutes) | TTP (minutes) | PE (° C.) |
|---|---|---|---|---|
| Trigonox 21 | 100 | 0.87 | 3.4 | 197 |
| Compound of Example 8 | 100 | 0.05 | 2.0 | 173 |

The peroxy ester according to the invention shows a much higher reactivity than Trigonox 21, which is highly desirable for applications such as pultrusion, as it increases the production speed and reduces the residence time. Also notable is the low peak exotherm, which is beneficial in reducing shrinkage and cracks.

The invention claimed is:

1. A process for the preparation of a monoperoxy ester or monoperoxy carbonate having one of the following formulae:

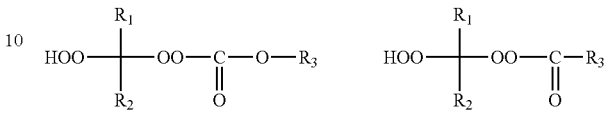

wherein $R_1$ and $R_2$ are independently selected from the group comprising hydrogen, $C_1$–$C_{20}$ alkyl, $C_3$–$C_{20}$ cycloalkyl, $C_6$–$C_{20}$ aryl, $C_7$–$C_{20}$ aralkyl, and $C_7$–$C_{20}$ alkaryl, which groups may include linear or branched alkyl moieties; and each of $R_1$ and $R_2$ may optionally be substituted with one or more groups selected from hydroxy, alkoxy, linear or branched alkyl, aryloxy, halogen, ester, carboxy, nitrile, and amido, and $R_3$ is independently selected from the group comprising $C_1$–$C_{20}$ alkyl, $C_3$–$C_{20}$ cycloalkyl, $C_6$–$C_{20}$ aryl, $C_7$–$C_{20}$ aralkyl, and $C_7$–$C_{20}$ alkaryl, which groups may include linear or branched alkyl moieties; and $R_3$ may optionally be substituted with one or more groups selected from hydroxy, alkoxy, linear or branched alkyl, aryloxy, halogen, ester, carboxy, nitrile, and amido, comprising the reaction of the corresponding ketone peroxide with the formula II:

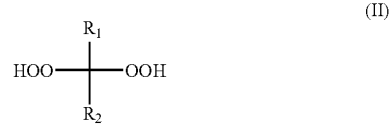

(II)

wherein $R_1$ and $R_2$ have the identified meaning, with an acid halogen or halogen formate of one of the following formulae:

wherein $R_3$ has the identified meaning, in an inert two-phase solvent system comprising polar solvents.

2. A process according to claim 1 wherein the polar organic solvent has a dipole moment of more than 0.5D.

3. A process according to claim 1 wherein the polar solvent is selected from alcohols, ethers, anhydrides, carbonates, cycloalkahols, alkylene glycols, amides, aldehydes, ketones, epoxides, esters, halogenated hydrocarbons, and mixtures thereof.

4. A process according to claim 1 wherein the equivalent amount of acid halogen or halogen formate is in the range of 0.5–5 equivalents.

5. A process according to claim 1 wherein the ketone peroxide is selected from the group consisting of methylethyl ketone, methylisopropyl ketone, methylisobutyl ketone, acetone, cyclohexanone, and 2,4,4-trimethyl cyclohexanone, and the acid chloride is selected from the group consisting of 2-ethylhexanoyl chloride, pivaloyl chloride, neodecanoyl chloride, neoheptanoyl chloride, isobutyryl chloride.

6. Monoperoxy carbonates having the formula

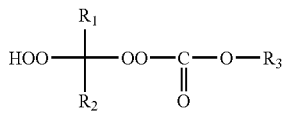

wherein $R_1$ and $R_2$ are independently selected from the group comprising hydrogen, $C_1$–$C_{20}$ alkyl, $C_3$–$C_{20}$ cycloalkyl, $C_6$–$C_{20}$ aryl, $C_7$–$C_{20}$ aralkyl, and $C_7$–$C_{20}$ alkaryl, which groups may include linear or branched alkyl moieties; and each of $R_1$ and $R_2$ may optionally be substituted with one or more groups selected from hydroxy, alkoxy, linear or branched alkyl, aryloxy, halogen, ester, carboxy, nitrile, and amido, and $R_3$ is independently selected from the group comprising $C_1$–$C_{20}$ alkyl, $C_3$–$C_{20}$ cycloalkyl, $C_6$–$C_{20}$ aryl, $C_7$–$C_{20}$ aralkyl, and $C_7$–$C_{20}$ alkaryl, which groups may include linear or branched alkyl moieties; and $R_3$ may optionally be substituted with one or more groups selected from hydroxy, alkoxy, linear or branched alkyl, aryloxy, halogen, ester, carboxy, nitrile, and amido, comprising the reaction of the corresponding ketone peroxide with the formula II:

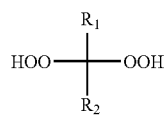

(II)

wherein $R_1$ and $R_2$ have the identified meaning, with an acid halogen or halogen formate of one of the following formulae:

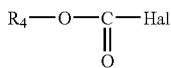 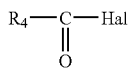

wherein $R_3$ has the identified meaning, in an inert two-phase solvent system comprising polar solvents.

7. A process for the preparation of diperoxy esters, diperoxy carbonates, and their mixed form peroxy ester peroxy carbonate having one of the following formulae:

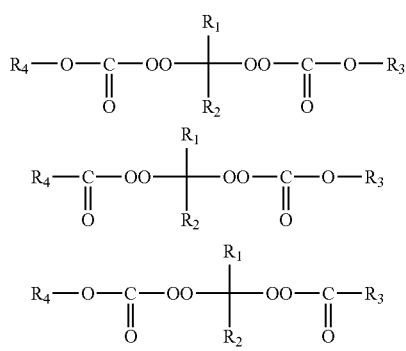

-continued

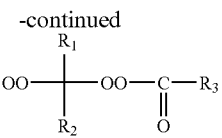

wherein $R_1$ and $R_2$ are independently selected from the group comprising hydrogen, $C_1$–$C_{20}$ alkyl, $C_3$–$C_{20}$ cycloalkyl, $C_6$–$C_{20}$ aryl, $C_7$–$C_{20}$ aralkyl, and $C_7$–$C_{20}$ alkaryl, which groups may include linear or branched alkyl moieties; and each of $R_1$ and $R_2$ may optionally be substituted with one or more groups selected from hydroxy, alkoxy, linear or branched alkyl, aryloxy, halogen, ester, carboxy, nitrile, and amido, and $R_3$ and $R_4$ areis independently selected from the group comprising $C_1$–$C_{20}$ alkyl, $C_3$–$C_{20}$ cycloalkyl, $C_6$–$C_{20}$ aryl, $C_7$–$C_{20}$ aralkyl, and $C_7$–$C_{20}$ alkaryl, which groups may include linear or branched alkyl moieties; and $R_3$ and $R_4$ may optionally be substituted with one or more groups selected from hydroxy, alkoxy, linear or branched alkyl, aryloxy, halogen, ester, carboxy, nitrile, and amido, comprising the reaction of a monoperoxy ester or monoperoxy carbonate having one of the following formulae:

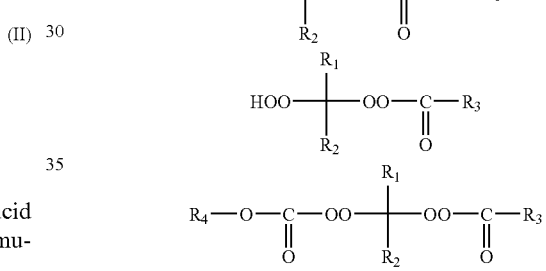

with an acid halogen or halogen formate with one of the following formulae:

wherein $R_4$ is as defined, in an inert two-phase solvent system comprising an apolar solvent.

8. A process according to claim 7 wherein $R_4$ is different from $R_3$.

9. Diperoxy esters and diperoxy carbonates, and their mixed form peroxy ester peroxy carbonate having one of the formulae:

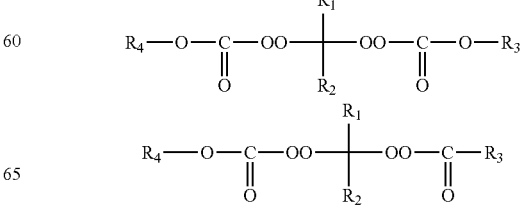

-continued

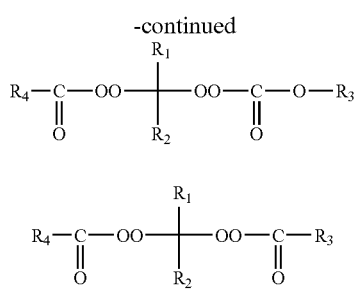

wherein wherein $R_1$ and $R_2$ are independently selected from the group comprising hydrogen, $C_1$–$C_{20}$ alkyl, $C_3$–$C_{20}$ cycloalkyl, $C_6$–$C_{20}$ aryl, $C_7$–$C_{20}$ aralkyl, and $C_7$–$C_{20}$ alkaryl, which groups may include linear or branched alkyl moieties; and each of $R_1$ and $R_2$ may optionally be substituted with one or more groups selected from hydroxy, alkoxy, linear or branched alkyl, aryloxy, halogen, ester, carboxy, nitrile, and amido, and $R_3$ and $R_4$ are selected from the group comprising $C_1$–$C_{20}$ alkyl, $C_3$–$C_{20}$ cycloalkyl, $C_6$–$C_{20}$ aryl, $C_7$–$C_{20}$ aralkyl, and $C_7$–$C_{20}$ alkaryl, which groups may include linear or branched alkyl moieties; and $R_3$ and $R_4$ may optionally be substituted with one or more groups selected from hydroxy, alkoxy, linear or branched alkyl, aryloxy, halogen, ester, carboxy, nitrile, and amido, with the proviso that $R_3$ is different from $R_4$.

10. The polymerization of monomers to form polymers in the presence of at least one peroxy ester, peroxy carbonate, or mixed diperoxide, as defined in any of claims 6 or 9 as a polymerization initiator; or the curing of unsaturated polyester in the presence of at least one peroxy ester, peroxy carbonate, or mixed diperoxide, as defined in claim 6, as a curing agent; or the modification of a polymer in the presence of at least one peroxy ester, peroy carbonate, or mixed diperoxide, as defined in claim 6, as a modifying agent.

11. A formulation comprising a peroxy ester, peroxy carbonate and/or mixed diperoxy, and mixtures thereof, as defined in claim 6, and a carrier or diluent.

12. A formulation according to claim 11 comprising the peroxy ester, peroxy carbonate and/or mixed diperoxide in an amount of 1.0–99% by weight.

13. A formulation according to claim 12 wherein the carrier or diluent is a solid, liquid, or paste.

14. A formulation according to claim 13 wherein the liquid is an apolar solvent.

15. A formulation according to claim 11 having the form of a dispersion.

16. A process according to claim 1 wherein the polar organic solvent has a dipole moment of more than 0.7D.

17. A process according to claim 1 wherein the polar organic solvent has a dipole moment of more than 1.0D.

18. A process according to claim 1 wherein the equivalent amount of acid halogen or halogen formate is in the range of 0.9–2 equivalents.

19. A process according to claim 1 wherein the equivalent amount of acid halogen or halogen formate is in the range of 0.9–1.5 equivalents.

* * * * *